United States Patent [19]
Romero et al.

[11] Patent Number: 5,109,713
[45] Date of Patent: May 5, 1992

[54] METHOD AND APPARATUS FOR TREATING AND STORING SULFUR CONTAINING GAS SO AS TO PROHIBIT THE DEGRADATION OF SAME

[75] Inventors: Irene Romero; Rui Rodrigues, both of Los Teques, Venezuela

[73] Assignee: Intevep, S.A., Caracas, Venezuela

[21] Appl. No.: 669,616

[22] Filed: Mar. 14, 1991

Related U.S. Application Data

[63] Continuation-in-part of Ser. No. 621,601, Dec. 3, 1990, abandoned.

[51] Int. Cl.$^5$ .............................. G01N 1/00
[52] U.S. Cl. ..................... 73/864.83; 55/35; 55/20; 55/73; 55/270; 55/387; 55/179; 55/275; 220/0.7
[58] Field of Search ............. 55/35, 73, 387–389, 55/270, 275, 179, 20; 73/864.81, 864.83, 864.91, 863.81; 206/0.6, 0.7

[56] References Cited

U.S. PATENT DOCUMENTS

| | | | |
|---|---|---|---|
| 1,798,733 | 3/1931 | Hasche | 55/73 |
| 1,892,428 | 12/1932 | Fonda | 55/19 |
| 2,699,837 | 1/1955 | Van Note | 55/179 |
| 2,715,450 | 8/1955 | Bliss et al. | 73/864.81 |
| 2,955,673 | 10/1960 | Kennedy et al. | 55/163 |
| 3,705,480 | 12/1972 | Wireman | 55/275 |
| 3,715,866 | 2/1973 | Chatlos et al. | 55/270 |
| 3,824,858 | 7/1974 | Erdman | 73/864.91 |
| 4,191,541 | 3/1980 | Jenkins | 55/270 |
| 4,927,038 | 5/1990 | Roebuck | 206/0.6 |
| 4,968,334 | 11/1990 | Hilton | 55/179 |

OTHER PUBLICATIONS

H$_2$S & SO$_2$ Removal by Charcoal Filtering, Emukai et al, Review of Elect. Comm Laboratories, vol. 21, No. 5,6 May Jun. 1973, pp. 384–390.

*Primary Examiner*—Bernard Nozick
*Attorney, Agent, or Firm*—Bachman & LaPointe

[57] ABSTRACT

A method and apparatus for treating gas samples containing sulfur comprises dehydrating the gas sample so as to obtain a dried gas sample having a water content of less than 100 ppm and thereafter storing the dried gas sample in a container which is non-reactive to sulfur in the gas.

28 Claims, 3 Drawing Sheets

METHOD AND APPARATUS FOR TREATING AND STORING SULFUR CONTAINING GAS SO AS TO PROHIBIT THE DEGRADATION OF SAME

CROSS REFERENCE TO RELATED APPLICATIONS

This application is a Continuation-In-Part of application Ser. No. 621,601, filed Dec. 3, 1990, now abandoned.

BACKGROUND OF THE INVENTION

The present invention is drawn to a method and apparatus for treating a gas sample containing sulfur and, more particularly, a method and apparatus for treating a gas sample containing sulfur so as to prohibit the degradation of the sulfur content of the gas sample over time when stored.

One of the major concerns facing industry today is the control of environmental pollution. One of the most harmful pollutants present in process gases used and/or produced by industry are sulfur compounds. The undesirability of sulfur compounds are exhibited not only in environmental pollution caused by burning of gas containing sulfur but also corrosion of plant and laboratory equipment which results from contact with sulfur compounds.

In light of the foregoing, it is highly desirable to be able to accurately analyze process gases and the like and their sulfur content in order to insure proper treatment of said gases so as to avoid the deleterious effects attributed to the sulfur in such process gases. To date, the sampling and storing of sulfur gases has remained an unsolved problem. The main reason for this is that the sulfur content of a gas sample which is being analyzed tends to degrade over time and, therefore, the value measured tends to be lower than the true value of the sulfur content of the gas actually being employed in various commercial situations. This decomposition of sulfur has been observed even at sulfur concentrations below 5% and occur in all types of gases whether they be natural gases, process gases or air.

The prior art has attempted to address the foregoing problem. "Methods of Sampling and Storage of Air containing Vapors and Gases", Int. J. Air. Poll., Vol. 2, pp. 142-158, 1959, quantifies several of the difficulties encountered in the storage of sulfur compounds including the difficulty of measuring concentrations of sulfur compounds as compared to various other compounds, and the fast decomposition time of the sulfur compounds over time. While it was found that the decomposition time of sulfur dioxide could be extended by proper choice of storage container, decomposition nevertheless occurs over a rather short period of time. Thus even with a proper choice of materials, effective long-term storage is not possible.

In addition to the difficulties of storing sulfur compounds, it is likewise difficult to accurately measure the concentration of sulfur compounds in gases. One of the most reliable alternatives available to date for the quantitative determination of sulfur content is the Drager method. Although the Drager method allows measurements to be made in the field, the method has several limitations: reduced accuracy, the method is sensitive to only some sulfur species, it requires a great deal of expertise by the operator, and optical interference appears whenever more than one sulfur compound is present. Further, the Drager method Provides no means for storage of the gas samples.

Other techniques have also been developed for the analysis of sulfur compounds.

Kimbell, U.S. Pat. No. 3,756,781 teaches a method of analyzing sulfur content in hydrocarbons by first breaking the hydrocarbons down into simpler molecular structures.

Sisti, U.S. Pat. No. 4,293,308 discloses a method and apparatus for determining very small percentages of sulfur in gas samples.

Overall, sulfur compounds in gases are very difficult to measure with time due to the breakdown of the compounds while in storage. Yet, as the harmful effects of these compounds appear from even very low concentrations, it is desirable to detect concentrations of sulfur in the parts per billion range. There exists a need for a simple method and apparatus to sample and store gases containing sulfur compounds with little or no breakdown of the compounds while in storage, so that sulfur concentrations can be accurately measured at later times. In addition, to be used more effectively, such an apparatus should be portable so that it may be moved to the supply of gas. There are many applications which require an accurate sulfur reading at later times, and none of the prior art suggests such a solution for this problem.

Accordingly, as aforementioned, it would be highly desirable to provide an efficient method and apparatus for treating sulfur containing gases so as to prohibit the degradation of the sulfur contained in the gases over time thereby allowing for an accurate measurement of the actual sulfur content of the gases.

Accordingly, it is a principal object of the present invention to provide a method and apparatus for storing sulfur containing gases so as to prohibit the degradation of the sulfur content of the gas over time.

It is a particular object of the present invention to provide a method as aforesaid wherein the sulfur containing gas is pretreated prior to storage so as to prohibit degradation of the sulfur content of same over time.

It is a still further object of the present invention to provide a storage container which is non-reactive to sulfur contained in a gas sample.

It is a further object of the present invention to treat a sulfur containing gas so as to prohibit the degradation of same over time by dehydrating the gas and storing the gas in non-reactive containers.

Further objects and advantages of the present invention will appear hereinbelow.

SUMMARY OF THE INVENTION

In accordance with the present invention, the foregoing objects and advantages are readily obtained.

The present invention is drawn to a method and apparatus for treating and storing gas samples containing sulfur and, more particularly, a method and apparatus for treating a gas sample containing sulfur wherein the degradation of the sulfur content of the gas sample over time is prohibited.

In accordance with the method of the present invention, a gas sample containing sulfur is subjected to dehydration so as to obtain a dried gas sample having a water content of less than 100 ppm. In accordance with the present invention, it has been found that the gas sample must be treated with a dehydrating agent in an amount of greater than or equal to 1.5 kg of dehydrating agent per liter of water to be removed from the gas sample.

The dehydrated dried gas sample is thereafter stored in a container which is non-reactive to the sulfur remaining in the gas and which is also water impermeable thereby prohibiting the reintroduction of water into the stored gas sample In accordance with the process of the present invention, the dehydrated agent employed in the process is selected from the group consisting of carbon, magnesium perchlorate, glycol, silica gel, alumina and mixtures thereof with magnesium perchlorate being preferred. In accordance with a further feature of the process of the present invention, the temperature, pressure and flow rate of the gas sample to the dehydration zone is maintained under controlled conditions so as to maximize the dehydrating effect of the dehydration agent on the gas sample.

The apparatus in accordance with the present invention comprises a dehydrating zone consisting of at least one trap containing a dehydrating agent through which the gas sample passes. In accordance with the preferred embodiment of the present invention, the dehydration zone comprises a plurality of traps which are selectively fed with the gas sample upon sensing of saturation of the dehydrant in any one of the traps. The apparatus of the present invention further includes the employment of storage containers which are non-reactive to sulfur contained in the gas sample and impermeable to water. The most preferred storage containers could be selected between aluminized plastic bags of the type sold under the Trademark Calibrated Systems, and Aluminium Cylinders with Spectra-Seal treatment sold under the Trademark Airco.

The method and apparatus of the present invention makes it possible to obtain accurate readings of the sulfur content of gas samples many days after the gas samples are withdrawn from their source. The improved accuracy allowed by the apparatus of the present invention has numerous benefits including (1) quality control in the production of natural gas, (2) accurate guarantees of qualities and composition of the natural gas to suppliers and purchasers, (3) reduced corrosion in transportation pipes and facilities employing the gases, and (4) reduction in harmful environmental consequences resulting from the use of said sulfur containing gases.

DETAILED DESCRIPTION

Figure 1:
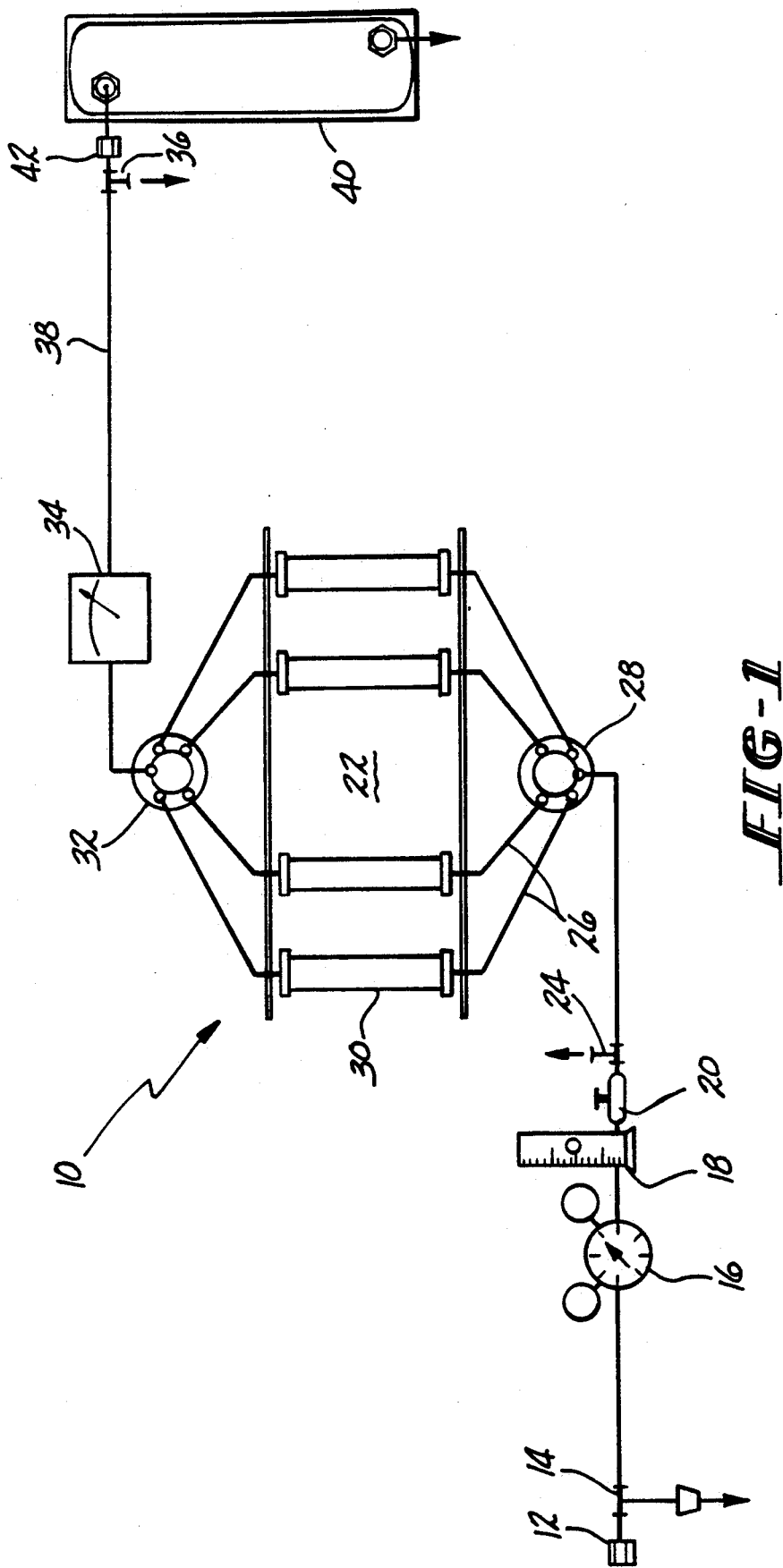
FIG. 1 is a schematic illustration of the apparatus and process of the present invention.

FIG. 1 is a schematic illustration of the system of the present invention for carrying out the method for dehydrating and storing sulfur containing gas samples without sulfur degradation over time.

The system 10 is provided with a connection 12 for tapping into a gas line and removing a gas sample therefrom. The gas sample might be generated from any source such as oil wells, environment, etc. Usually, depending on the source, the moisture content of the sample may be as high as 20,000 ppm water and the sulfur content could be as low as 10 ppm. The gas is permitted to flow through the pipe 14, a steel Teflon type pipe preferably, to which are connected successively a metering means 16 for regulating the pressure, a thermometer 18 for measuring the temperature and a metering means 20 to control the flow rate of the gas to a dehydrating zone 22. The gas samples are preferably at a pressure between 10 and 100 psi, temperatures no higher than 60° C. and a flow rate from 0.2 to 2.0 l/min. The reason why these parameters have to be maintained at the aforesaid values are the following: (1) at pressures higher than 40 psi the dehydrating apparatus would need to be reinforced; (2) at temperatures higher than 60° C., the grain shape of the dehydration agent used in the method would deteriorate and consequently would not be effective for dehydration purposes; and (3) at higher flow rates, the gas sample would not have enough residence time with the dehydration agent to effect the required dehydration. The dehydration agent may be selected from a group of well known substances such as silica gel, alumina, magnesium perchlorate, activated carbon, glycol, and mixtures thereof with magnesium perchlorate being most preferred.

Pipe 14 is also provided upstream of elements 16, 18 and 20 with a drainage valve 24 which is used for removing from the system all liquids which may be present in the gas sample. Most natural gases contain a liquid phase which consists basically of $C_6$-$C_{14}$ fractions which are carried with the gas. The liquid phase arises due to condensation which occurs by expansion effects due to the pressure difference between the main gas line and the system.

The valve 24 has two positions for (a) connecting the flow line 14 with the dehydration zone 22 or for (b) connecting the flow line 14 with atmosphere so that the three parameters (temperature, pressure and flow rate) can be controlled and excess gas pressure can be released out of the system. It must be appreciated that the system of the invention is a dynamic system which means the gas flows constantly through the whole system. With the valve 24 in position (b), it is possible to measure the sulfur content of the gas sample to obtain a reference value of the sulfur content so that the sulfur content measured after the dehydration and every several days storage can be compared and the performance of the system can be evaluated. The sulfur content is measured in known manner by connecting to valve 24 a DRAGER tube. With the valve 24 in position (a), the gas sample is allowed to reach the distribution valve 28. Valve 28 is a single-inlet, multiple-outlet type valve and preferably a five way type valve. The distribution valve 28 allows the gas samples to be selectively directed to any of a plurality of plexiglass traps 30 which are filled with the dehydration agent to be used in the invention for removing or reducing the moisture content of the gas sample. Each outlet of said distribution valve 28 is connected to one plexiglass trap 30 by lines 26 so that only one trap 30 is in use at any one time. Thus, the number of plexiglass traps 30 correspond to the number of outlets on distribution valve 28. In a preferred embodiment of this invention, just one of the traps 30 is used for dehydrating a gas sample flowing through it; however, if necessary, it is possible to use a plurality of plexiglass traps 30. The feature which is critical is that the gas samples leaving the traps 30 must have a moisture content below 100 ppm as it will be demonstrated hereinafter.

Distribution valve 32 which is a multiple inlet-single outlet type valve connects each trap 30 with a moisture meter 34 the gas sample is measured.

The saturation point of the dehydrating agent in any one of the traps 30 can be observed at said moisture meter 34 by measuring the moisture content of the gas leaving the trap. When the saturation point of the agent in a trap is approached, one turns the distribution valve 28 in order to direct the gas flow from trap 30 filled with the saturated dehydrating agent to another trap 30 filled with unused dehydrating agent. The ratio of dehydration agent to water content in the gas sample must be maintained higher than 1.50 kg/lt in order to obtain effective dehydration within the designed system. The valve 36 is provided downstream of the moisture meter 34 for (a) connecting the flow line 38 coming from the moisture meter 34 with storage tank 40 or for (b) connecting the system with atmosphere in order to reduce pressure in the system. Valve 36 in position (a) controls the volume of gas flowing into the container 40. The container 40 to be used in the invention is connected to the rest of the system by means of the air-tight connecting device 42. The containers used in the apparatus and method of the present invention are selected based on materials which have no capacity for reacting with sulfur and which are not water permeable so as to raise the water content of the sulfur during storage. The containers preferably used in this invention are plastic bags with aluminized outside and aluminum cylinders coated with plastic such as epoxy or the like.

EXAMPLE I

In order to demonstrate the effect of water content on the degradation of sulfur in a gas sample when stored, a natural gas sample having a water content of 100 ppm was treated in accordance with the method of the present invention. The natural gas having a water content of 100 ppm is considered to be a very dry gas sample compared to typical natural gas samples. The gas sample was fed at a pressure of 30 psi, a temperature of 55° C. and a flow rate of 1.5 liters per minute to a dehydration zone containing magnesium perchlorate. The magnesium perchlorate in the reaction zone was present in an amount sufficient to reduce the water content of the gas sample by approximately 90%, that is, in an amount of 1.50 kg per liter of water be removed. The sulfur content of the dehydrated dry gas sample was measured and found to be 12 ppm.

Figure 2:
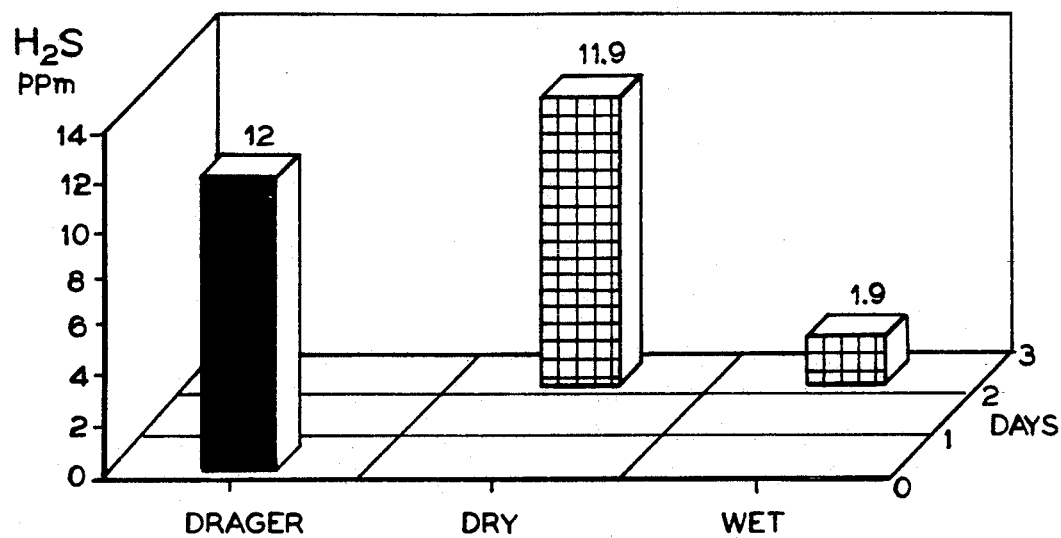
FIG. 2 is a graph illustrating the degradation of sulfur over time in wet and dehydrated gas samples.

The dry gas sample was thereafter fed to an aluminized storage container having the interior surface thereof electrolytically coated. The cylinder is a commercially available cylinder sold by Airco. An untreated gas sample having the water content of 100 ppm was likewise stored in an identical storage container. After three (3) days of storage, the sulfur content of the gas samples was again measured and the sulfur content of the treated dehydrated gas sample was measured to be 11.9 ppm which is virtually identical to that of the original dehydrated gas sample whereas the sulfur content of the non-treated wet gas sample having an original water concentration of 100 ppm was found to be 1.9 ppm. This example clearly illustrates the benefit of treating by dehydration prior to storing on the degradation of sulfur in gas samples. The results are graphically illustrated in FIG. 2.

EXAMPLE II

Figure 3:
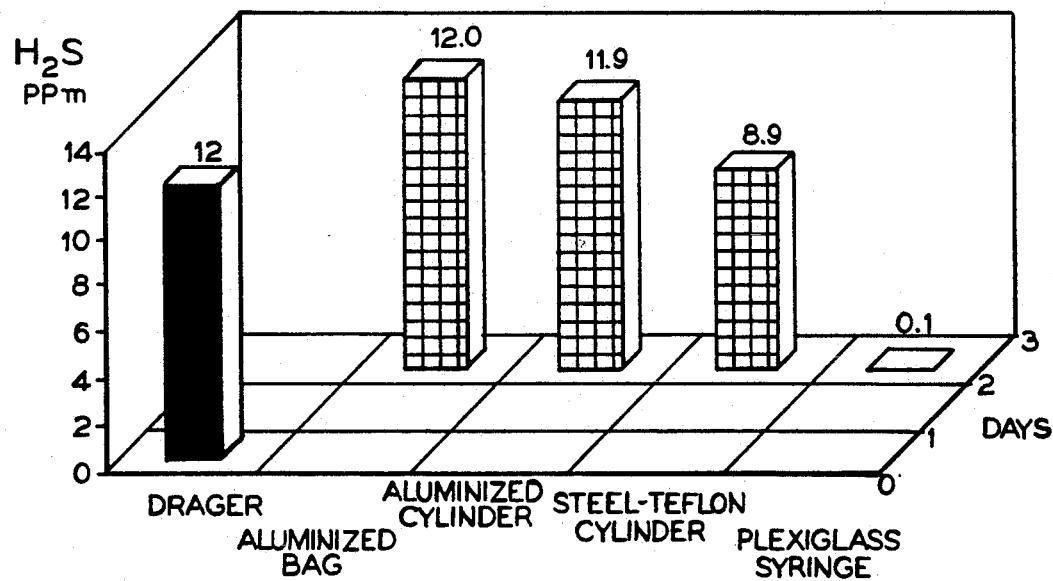
FIG. 3 is a graph showing the effect of various storage containers on the degradation of sulfur in dehydrated gas samples.

Example II was carried out to demonstrate the effect of storage containers on the degradation of sulfur over time when stored. In this example, the gas sample of Example I which was dehydrated was stored in three (3) different containers. The first container is an aluminized plastic bag sold by Calibrated Systems. The second sample was stored in a Teflon coated steel cylinder. The third sample was stored in a plexiglass syringe sold by Hamilton. As can be seen in FIG. 3, the sample stored in the Calibrated System's aluminized bag showed less deterioration than the sample stored in the aluminized cylinder of Example 1. The sample stored in the Teflon coated steel cylinder was slightly inferior to both the aluminized bag and the aluminium cylinder. The sample stored in the plexiglass syringe sold by Hamilton showed nearly total sulfur degradation after a time of three (3) days. This example illustrates that the preferred storage container for prohibiting the degradation of sulfur in a gas sample is the aluminized bag container sold by Calibrated Systems.

EXAMPLE III

Figure 4:
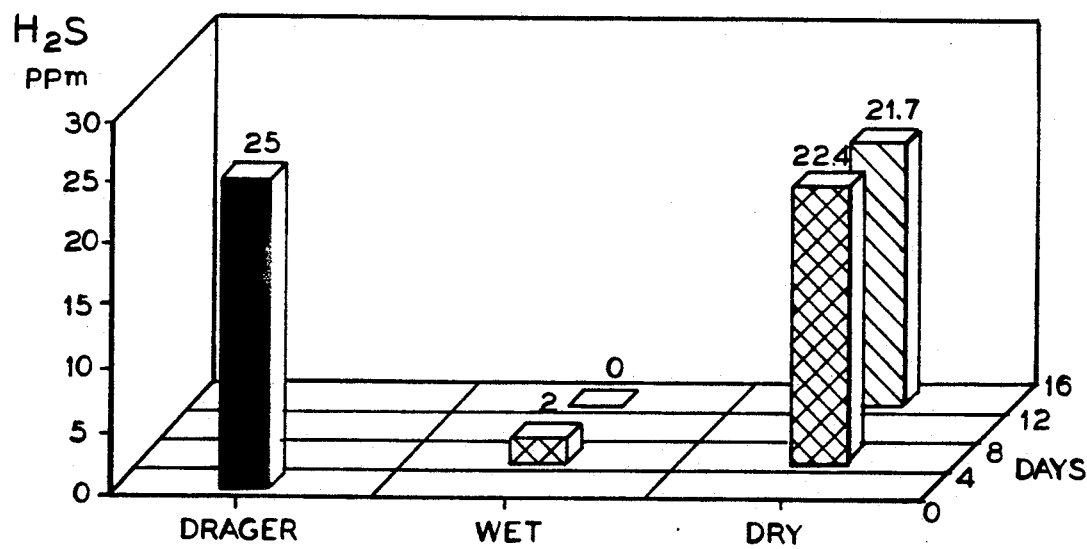
FIG. 4 is a graph further illustrating the effect of storage containers on the degradation of dehydrated gas samples over time.

Again, in order to demonstrate the advantages of the process of the present invention, and particularly the effect of dehydration on the degradation of sulfur over time, a further test was conducted wherein a gas sample having a sulfur content of 25 ppm was stored in the preferred aluminized bag discussed above with reference to Example II. A wet gas sample having a water content of 15,000 ppm was likewise stored in another aluminized bag. The sulfur content of both samples were measured after eight (8) days and again after sixteen (16) days. As can be seen in FIG. 4, the sample content of the wet gas sample totally degraded in terms of sulfur content after sixteen (16) days as compared to the gas sample treated in accordance with the process of the present invention which had a reduced sulfur concentration of less than 20%.

The foregoing examples clearly demonstrate the positive effect of the process of the present invention on prohibiting the degradation of sulfur in a gas sample over time when stored in optimum storage containers.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A method for treating a sulfur gas containing gas sample to be later analyzed so as to prohibit the degradation of the sulfur gas content of the gas sample over time comprising the steps of:
    a) providing a sulfur gas containing gas sample;
    b) dehydrating said gas sample so as to obtain a water content in said gas sample of less than 100 ppm to produce a dried gas sample;
    c) storing said dried gas sample in a container which is non reactive with the sulfur gas in the dried gas sample; and
    d) thereafter removing and analyzing said dried gas sample for sulfur gas content.

2. A method according to claim 1 wherein said gas sample has a water content of up to 20,000 ppm.

3. A method according to claim 1 including the step of removing any liquid phase from said gas sample prior to the step of dehydrating.

4. A method according to claim 1 including the step of measuring the moisture content of said gas sample prior to the step of dehydrating.

5. A method according to claim 1 including the step of measuring the sulfur content in said gas sample prior to the step of dehydrating.

6. A method according to claim 1 wherein dehydrating said gas sample comprises the steps of:
providing a dehydration zone, allowing said gas sample to flow through said dehydration zone.

7. A method according to claim 6 wherein said dehydration zone comprises at least one plexiglass trap filled with a dehydration agent.

8. A method according to claim 7 wherein said dehydration agent is selected from the group consisting of carbon, magnesium perchlorate, glycol, silica gel, alumina and mixtures thereof.

9. A method according to claim 7 including measuring the water content of said gas sample downstream of said at least one plexiglass trap.

10. A method according to claim 1 further comprising the steps of:
regulating the temperature, pressure and flow rate of said gas sample prior to the dehydrating step.

11. A method according to claim 10 wherein said temperature is less than or equal to 60° C., said pressure is from 10 to 100 psi and said flow rate is from 0.2 to 2.0 l/min.

12. An apparatus for treating a sulfur gas containing gas sample so as to prevent a change in sulfur gas content over time when stored which apparatus comprises:
means for obtaining a gas sample containing sulfur gas;
conduit means for transporting said gas sample to a dehydration zone;
means for dehydrating said gas sample in said dehydration zone thereby producing a dried gas sample with a water content up to 100 ppm;
conduit means for transporting said dried gas sample to a storage container;
means for storing said dried gas sample in said storage container wherein said container is non reactive with the sulfur gas in the dried gas sample; and
means for removing and analyzing said dried gas sample for sulfur gas content.

13. An apparatus according to claim 12 including means for regulating the pressure of said gas sample;
means for measuring the temperature of said gas sample; and
means for regulating the flow rate of said gas sample.

14. An apparatus according to claim 12 including means for removing a liquid portion from said gas sample.

15. An apparatus according to claim 12 wherein said storing means comprises an aluminized plastic bag.

16. An apparatus according to claim 12 wherein said storing comprise a pretreated aluminum cylinder.

17. An apparatus according to claim 12 wherein said means for dehydrating comprises a dehydration zone having at least one plexiglas trap containing a dehydration agent.

18. An apparatus according to claim 17 wherein said dehydration agent is selected from the group consisting of carbon, glycol, magnesium perchlorate, silica gel and alumina.

19. An apparatus according to claim 12 wherein said dehydrating agent means further comprises:
means for distributing said gas samples to only one of said plexiglass traps, and
means for collecting said dried gas sample from only one of said plexiglass traps.

20. An apparatus according to claim 19 wherein said distributing means comprises a single-inlet, multiple outlet valve, and said collecting means comprises a multiple-inlet, single outlet valve.

21. An apparatus according to claim 19 further including a moisture meter to measure the moisture content of said dried gas sample.

22. A method for treating a sulfur gas containing gas sample to be later analyzed so as to prohibit the degradation of the sulfur gas content in the gas sample over time comprising the steps of:
a) providing a sulfur gas containing gas sample having a known water content;
b) contacting said gas sample with a dehydrating agent in an amount of greater than or equal to 1.50 kg of said dehydrating agent per liter of water to be removed from said gas sample so as to obtain a dried gas sample;
c) storing said dried gas sample in a container which is non reactive with the sulfur gas in said dried gas sample; and
d) thereafter removing and analyzing said dried gas sample for sulfur gas content.

23. A method according to claim 22 wherein water content of said gas sample is up to 20,000 ppm.

24. A method according to claim 22 wherein said dehydration agent is selected from the group consisting of carbon, magnesium perchlorate, glycol, silica-gel and alumina.

25. A method according to claim 22 wherein the water content remaining in said dried gas sample is measured in order to determine when said dehydration agent is saturated.

26. A method according to claim 22 further comprising the step of removing any liquid phase from said gas sample prior to the step of dehydrating.

27. A method according to claim 22 wherein the the temperature and the flow rate of said gas samples are measured prior to contacting said gas sample with said dehydrating agent.

28. A method according to claim 27 wherein said pressure is from 10 to 100 psi, said temperature is lower than or equal to 60° C. and said flow rate is from 0.2 to 2.0 l/min.

* * * * *

UNITED STATES PATENT AND TRADEMARK OFFICE
CERTIFICATE OF CORRECTION

PATENT NO. : 5,109,713
DATED : May 5, 1992
INVENTOR(S) : Irene Romero et al.

It is certified that error appears in the above-identified patent and that said Letters Patent is hereby corrected as shown below:

In column 8, claim 16, line 2, after "storing" insert --means--.

In column 8, claim 27, line 1, after "the" first occurrence insert --pressure,--.

Signed and Sealed this

Eleventh Day of January, 1994

Attest:

BRUCE LEHMAN

Attesting Officer    Commissioner of Patents and Trademarks